(12) United States Patent
Robinson (10) Patent No.: US 6,238,214 B1
(45) Date of Patent: *May 29, 2001

(54) GUIDED TISSUE REGENERATION PLATE FOR USE IN A PROCESS FOR GROWING JAW BONE IN ANTICIPATION OF PERFORMING DENTAL IMPLANTS

(76) Inventor: Dane Q. Robinson, 6015 E. Quartz Mountain Rd., Paradise Valley, AZ (US) 85253

( * ) Notice: Subject to any disclaimer, the term of this patent is extended or adjusted under 35 U.S.C. 154(b) by 0 days.

This patent is subject to a terminal disclaimer.

(21) Appl. No.: 09/196,915

(22) Filed: Nov. 20, 1998

Related U.S. Application Data

(63) Continuation-in-part of application No. 08/609,870, filed on Mar. 1, 1996, now Pat. No. 5,839,899.

(51) Int. Cl.⁷ ............................. A61C 8/00; A61F 2/28; A61L 31/00

(52) U.S. Cl. ..................... 433/215; 433/173; 623/17.17

(58) Field of Search .................................. 433/167, 173, 433/174, 215; 623/16, 17.17

(56) References Cited

U.S. PATENT DOCUMENTS

| | | | |
|---|---|---|---|
| 4,961,707 | | 10/1990 | Magnusson et al. . |
| 5,196,016 | * | 3/1993 | Buser et al. . |
| 5,297,563 | | 3/1994 | Syers . |
| 5,372,503 | * | 12/1994 | Elia ...................... 433/215 |
| 5,380,328 | | 1/1995 | Morgan . |
| 5,489,305 | * | 2/1996 | Morgan .................. 623/16 |
| 5,511,565 | * | 4/1996 | Syers .................... 433/229 |
| 5,525,646 | * | 6/1996 | Lundgren et al. ....... 623/12 |
| 5,700,479 | * | 12/1997 | Lundgren ............... 623/11 |
| 5,727,945 | * | 3/1998 | Dannenbaum ......... 433/215 |
| 5,839,899 | * | 11/1998 | Robinson ............... 433/215 |

FOREIGN PATENT DOCUMENTS 0 574 091 * 12/1993 (EP) .
94/03121 * 2/1994 (WO) .

OTHER PUBLICATIONS

Scantlebury, Todd *1982–1992: A Decade of Technology Development for Guided Tissue Regeneration*, J. Periodontol, Nov. 1993 (Supp). vol. 64, No. 11 pp 1129–1137.*

* cited by examiner

Primary Examiner—Ralph A. Lewis
(74) Attorney, Agent, or Firm—Michael A. Lechter; David E. Rogers; Squire, Sanders & Demsey (57) ABSTRACT

A method of growing jaw bone and the related guided-tissue regeneration plate support and fixation system employed in the method where an isolated and protected space free from tissue impingement, occlusal loading, chewing forces or muscular pressure is created between the periosteum and the jaw bone. This space is created by first placing either a dental implant or a guided-tissue regeneration plate support and fixation system tenting-type support screw into the jaw bone. The plate portion of the guided-tissue regeneration plate support and fixation system, preferably made out of titanium, is a two-piece structure including a first support plate component having a peripheral region and a generally open central portion and a fine mesh screen juxtaposed over the central portion of the support plate and fixed to the peripheral region thereof. Alternatively, a titanium blank can be controllably etched to obtain reduced thickness central regions which, along with the original thickness regions, are methodically pierced to obtain numerous apertures to achieve the desired porosity for the central regions and the desired strength and pliability of the peripheral regions. The guided-tissue regeneration plate is either snapped-down onto the head of the support screw or onto a specialized and modified healing screw of a dental implant which has a receiver cap or is screwed directly into a dental implant. The plate is then bent and molded into the proper shape to provide the protected space.

47 Claims, 8 Drawing Sheets

GUIDED TISSUE REGENERATION PLATE FOR USE IN A PROCESS FOR GROWING JAW BONE IN ANTICIPATION OF PERFORMING DENTAL IMPLANTS

CROSS REFERENCE TO RELATED APPLICATION

This is a Continuation-in-Part of U.S. patent application Ser. No. 08/609,870, filed Mar. 1, 1996, by Dane Q. Robinson and entitled METHOD AND APPARATUS FOR GROWING JAW BONE UTILIZING A GUIDED-TISSUE REGENERATION PLATE SUPPORT AND FIXATION SYSTEM, now U.S. Pat. No. 5,839,899.

FIELD OF THE INVENTION

This invention relates to the art of dentistry and, more particularly, to devices which relate to the surgical placement of endosseous dental implants in the maxillary or mandibular jaw bone. Still more specifically, this invention relates to the growing of jaw bone in order to obtain adequate volume of osseous structure by using a thin titanium bone plate/screen which is mated to an underlying support bone screw or to a dental implant.

BACKGROUND OF THE INVENTION

The successful placement of endosseous dental implants has been well documented for over 30 years; however, the success of these endosseous dental implants has been limited by the quality and quantity of existing bone a given patient would present with. Due to the destructive nature of dentures to the underlying jaw bone as well as to the fact that bone that is not internally stimulated by tooth roots will atrophy, the amount of bone in many people is very limited for the placement of dental implants, especially for those who have been missing teeth for an extended period of time.

Bone grafting has become an essential element for the successful treatment of those who do not have enough bone for dental implants. As viable methods, blocks of hip bone have been affixed to the jaw, and freeze-dried demineralized bone protein has been used as a stimulant to cause the patient's bone cells to become active and lay down new bone onto the existing bone areas and into the new bone graft areas. Through experience and research, it has become evident that, for bone grafting to be successful, it must be given an isolated space to grow, protected from muscular pressure, tissue impingement and chewing forces. In order to create this space, many approaches have been proposed. For example, both Syers (U.S. Pat. No. 5,297,563) and Magnusson et al (U.S. Pat. No. 4,961,707) teach the use of a fabric-like membrane which is used over a bony defect. Although this barrier creates an isolated space from the invasion of epithelial cells into the bony defect or bone graft area, it does not create a protected space from chewing forces or tissue pressure.

Morgan (U.S. Pat. No. 5,380,328) teaches the use of a composite perforated titanium mesh layered with polytetrafluoraethylene (PTFE or Teflon®) fibers. Even though this approach would be feasible for creating a protected space in order to grow bone, it has some severe limitations. This material requires the placement of peripheral bone screws into the edges of the meshed piece in order to create a direct fixation of the titanitum mesh to the jaw bone and then bowing-up or tenting-up the center area in order to create the protected space. Often, it would not be feasible to place the peripheral bone screws in the peripheral areas for fear of damage to the inferior alveolar nerves or sinus penetration or damage to nearby tooth roots. The protrusion of these screws above the mesh is also of concern as potentially causing a tissue irritation complication with this given procedure.

Furthermore, the difficulty of forming the exact amount of tenting desired with this material is inherently very difficult to control. Additionally, the removal of this material is complicated by the need to surgically dissect much deeper to locate the peripheral screws. This technique would also be expensive and time consuming to emplace due to the need for multiple screws to secure a single mesh On the other hand, as will become more apparent below, the guided-tissue regeneration plate support and fixation system contemplated in accordance with the subject invention obtains the ability to place a single screw in the center of the bone graft area, thereby facilitating the selection of a screw height that allows for an exact amount of tenting, thus giving the support where it is needed most. Placement and removal of this device is greatly simplified due to the fact that peripheral screws are not required (although such can be used). The head of the screw ends up being mostly under the plate, thus preventing any concern about screw-head irritation or prousion. Furthermore, concern about danage to neighboring peripheral structures is eliminated. In general, a much more simplified and cost effective method, apparatus and result are achieved.

Experience with and further development of the guided-tissue regeneration plate support and fixation system has resulted in an important advance which enhances its effectiveness in practice. It has been found that the use of a fine mesh screen spanning open areas of a guided-tissue regeneration support plate results in a faster and more complete bone regeneration of the underlying bony ridge and faster and more healthy growth of the overlying periosteum. The fine mesh screen can be fabricated from any suitable material, resorptive or non-resorptive, and an especially suitable material especially when a titanium guided-tissue support plate is employed, is fine mesh screen titanium fixed to the support plate by welding, particularly spot or laser welding, by an adhesive or by sintering the two-piece assembly. Alternatively, a functional equivalent to a fine mesh screen region can be obtained by substantially reducing the thickness of predetermined central areas of an imperforate titanium (for example) plate and then perforating the reduced thickness regions with finely spaced apertures.

OBJECTS OF THE INVENTION

It is therefore a broad object of my invention to provide an improved dental implant system.

It is a more specific object of my invention o provide an improved dental implant system which is relatively inexpensive to fabricate and use.

In another aspect, it is an object of my invention to provide a dental implant system which is relatively easy to use to obtain high quality results.

SUMMARY OF THE INVENTION

Briefly, these and other objects of the invention are achieved by a method of growing additional maxillary or mandibular bone in areas of atrophy and by the use of a related device to accomplish the task. A pliable guided-tissue regeneration plate, which holds it shape after being bent, is employed as a mating component to a support screw or a dental implant and is secured to the jaw structure by fixation of the guided-tissue regeneration plate at a predetermined distance above or away from the surface of the bone to the support screw or dental implant in order to create a supported and protected space between the underside of the gum tissue and the original bone which is free from muscular and chewing pressure in order to promote bone growth.

The guided-tissue regeneration plate support and fixation system can be mated with a support screw or screws which are tenting screws designed to be mated with and then become intimately a part of the guided-tissue regeneration plate in order to grow bone in the space created by the guided-tissue regeneration plate system prior to implant placement. Additionally, the guided-tissue regeneration plate system can be utilized during implant placement by creating space adjacent to a dehisced implant by fixation of the guided-tissue regeneration plate directly to the implant in order to grow bone height or width. A guided-tissue regeneration plate according to the present invention can also be used by affixing it to an existing dental implant that has been previously placed and has undergone bone loss in order to regenerate new bone. The guided-tissue regeneration plate support and fixation system is adapted to be surgically removed after the bone has grown under its surface at a later uncovering or implant placement surgery. In an alternative preferred embodiment which provides particularly successful results and which results in faster and better bone regeneration and periosteum growth, the guided-tissue regeneration plate consists of first and second integrated components including a first support plate component having a peripheral region and a generally open central portion and a fine mesh screen juxtaposed over the central portion and fixed to the peripheral region thereof In a functionally equivalent variant of the alternative preferred embodiment, the guided-tissue regeneration plate is fabricated starting with an imperforate plate (for example, of titanium) and then reducing the thickness of predetermined central regions of the plate, a step which can be carried out, for example, by employing a conventional photo-resist mask over the plate in conjunction with an acid etch. After the desired thickness of the central regions has been obtained, the central regions may be perforated with finely spaced apertures using, for example, conventional laser machining techniques.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DETAILED DESCRIPTION OF THE PREFERRED EMBODIMENTS

The described invention relates to a method of growing jaw bone and to the related guided-tissue regeneration plate support and fixation system by which an isolated and protected space free from tissue impingement, occlusal loading, chewing forces, or muscular pressure is created between the periosteum and the jaw bone. This space is created by first placing either a dental implant or a guided-tissue regeneration plate support and fixation system tenting-type support screw into the jaw bone and then coupling the guided-tissue regeneration plate to the support screw.

The presently preferred embodiment of the support screws, preferably made out of (but not limited to) titanium, are thin shafted screws with a relatively high ratio between the greater diameter to the minor diameter of the threads to give the maximum bite and hold into the bone. Preferably, this ratio is at least two. The head of the tenting-type support screw is placed above or away from the bone a suitable distance of the space created in order to grow bone. The screw head is configured to receive the guided-tissue regeneration plate, thus allowing for most of the head to be either in or under the guided-tissue regeneration plate after it is engaged into a receiver cap of the head.

In another contemplated embodiment of the support screws, the head of the support screw is internally axially threaded or is provided with a threaded or non-threaded well allowing for a pin with a small head resembling a micro thumbtack to extend through the guided-tissue regeneration plate into the well and snap or thread into place, thereby securing the guided-tissue regeneration plate to the head of the tenting-type support screw. The support screw is preferably fabricated to be very sharp at its tip which includes a self-starting flute in order to facilitate self-threading for facilitating placement.

The guided-tissue regeneration plate is preferably made of thin titanium sheet metal having a peripheral thickness of around 5 to 10 thousandths of an inch. This thickness allows for the material to be thin enough to be bent into shape, but rigid enough to hold its shape after being bent and molded. The present material of choice is Grade 1 titanium which is the fully annealed form of titanium advantageously characterized in that it will not spring back after being bent.

The plates are fabricated with a precise aperture proximate the center or wherever needed in order to allow for a precise union and mating to the support screw or receiver cap of the healing screw of a dental implant, thus giving a secure fixation, by indirect means, to the jaw bone. The central area of the guided-tissue regeneration plate is preferably thicker in order to provide more support and rigidity than the peripheral region. The combination of the support screw and the thicker area of the plate near the center prevents the guided-tissue regeneration plate from caving-in in the area where maximum support is needed when overlying pressure, such as muscular pressure, chewing forces, or any other premature loading onto the guided-tissue regeneration plate support and fixation system, is later applied.

The guided-tissue regeneration plate can optionally be perforated to allow for better overlying tissue healing as well as to promote the exchange of nutrients and blood supply between the bone graft and the overlying tissue. Generally, the central, thicker, more supportive area is not perforated to obtain more support. Typically, the number and size of the perforations is less concentrated than the amount of solid space to create a more supportive plate at a thinner dimension. If a completely imperforate barrier is desired to isolate all transfer of unwanted epithelial cells into the bone graft area, then the guided-tissue regeneration plate is fabricated imperforate except for the generally centrally disposed aperture for fixing the plate to its support screw.

However, if a temporary period of isolation from epithelial cells is desired to create a membrane barrier from epithelial cells for a limited period of time which allows for the exchange of nutrients, ions, and tissue fluid or perhaps blood supply, then a resorptive barrier such as Vicryl™, collagen, resorptive hydroxyapatite crystals or Guidor™ can be applied to the under or over side of the guided-tissue regeneration plate to seal the perforations, then resorbing a limited time later after the system is installed.

If a non-resorptive semi-permeable result is desired, then the perforations can be covered by applying a suitable material such as PTFE fibers. After a period of several months have passed, the entire system is removed and then the implants are either simultaneously placed during this surgery or uncovered by placing healing caps into the implants. If the only desired effect is to create a better ridge for the stabilization of a denture, then the system may be left in place indefinitely.

Having now discussed the fundamentals of the present invention, attention is invited to the several FIGS. for an alternative and clarifying disclosure as the discussion proceeds.

Figure 1:
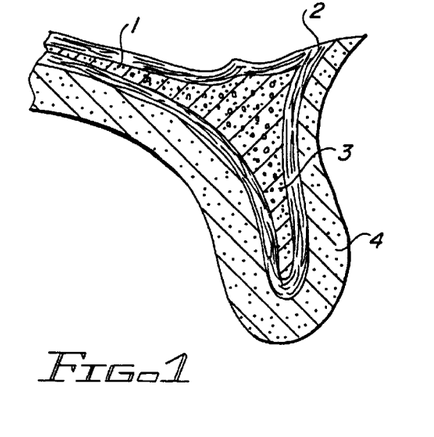
FIG. 1 illustrates a bony ridge that has undergone substantial loss.

FIG. 1 shows an exemplary existing midline cross-section of a maxillary edentulous ridge which has undergone substantial bone loss. For orientation purposes, landmarks can be identified by the palatal bone 1, the floor of the nose 2, the bony ridge 3, and the gum tissue 4.

Figure 2:
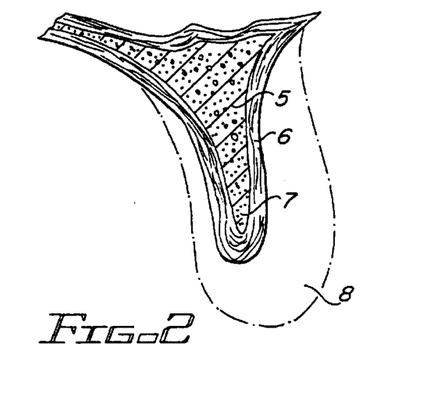
FIG. 2 depicts a cross-section of a maxillary midline area of an edentulous ridge showing the original size prior to bone loss.

FIG. 2 depicts a cross-section of a maxillary midline area of an edentulous ridge showing the original size prior to bone loss (the gum tissue is not shown in this view). Reference is taken to the marrow space 5, the cortical bone 6 and the current size of the ridge 7 after bone loss and to the area of the original size 8 of the ridge prior to atrophy or bone loss.

Figure 3:
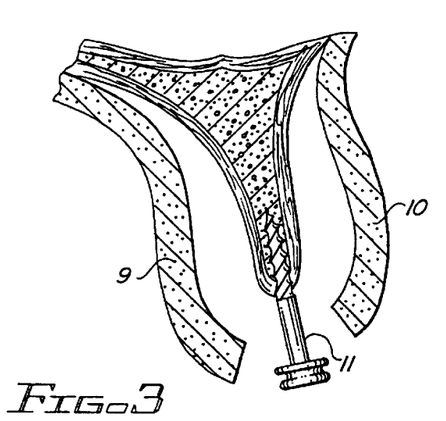
FIG. 3 shows the surrounding tissue first reflected away from the bony ridge to expose the ridge in its entirety.

Referring now to FIG. 3, in order to place a guided-tissue regeneration plate support and fixation system according to the present invention, the tissue is first reflected away from the bony ridge to expose the ridge in its entirety. The palatal gum tissue 9 is reflected, the facial gum tissue 10 is reflected, and a guided-tissue regeneration plate support screw 11 is placed into the bony ridge.

Figure 4:
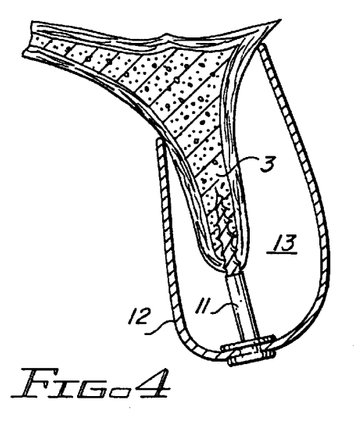
FIG. 4 depicts the mating of a guided-tissue regeneration plate component of the invention to a support screw component of a snap-fit embodiment.

FIG. 4 depicts the mating of the guided-tissue regeneration plate 12 to a guided-tissue regeneration support screw 11 of the snap-fit embodiment. (The gum tissue is not shown.) The space 13 is the area where new bone will grow, the space having been created by the guided-tissue regeneration plate support and fixation system of the invention. The guided-tissue regeneration plate support screw 11 is placed into the bony ridge 3. After the guided-tissue regeneration plate 12 is affixed to the guided-tissue regeneration plate support screw 11 by snapping it in place, the plate is molded into shape by bending the edges down as shown.

Figure 5:
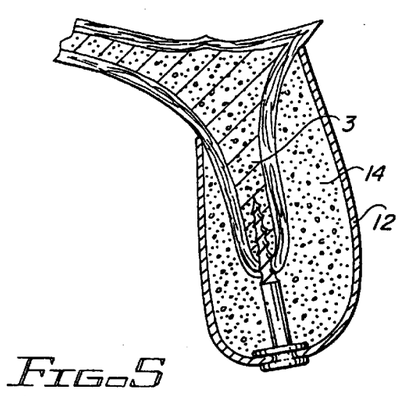
FIG. 5 shows bone graft material packed beneath the plate and against the existing bony ridge.

As shown in FIG. 5, once the guided-tissue regeneration plate 12 has been molded into place, then bone graft material 14 is packed beneath the plate 12 and against the existing bony ridge 3. After a period of approximately four-to-eight months, a new bony ridge will form within the space created by the guided-tissue regeneration plate support and fixation system. (Gum tissue not shown.)

Figure 6:
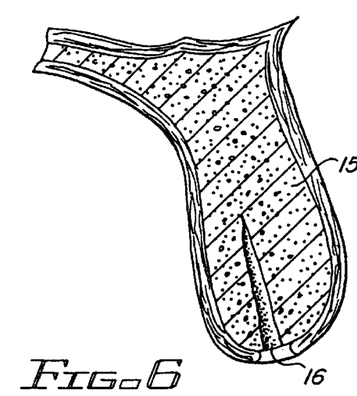
FIG. 6 shows how the bony ridge appears after the guided-tissue regeneration plate support and fixation system has been removed to expose the new bony ridge.

Thus, FIG. 6 shows how the bony ridge appears after the guided-tissue regeneration plate support and fixation system has been removed to expose the new bony ridge 15. A small hole 16 remains after the removal of the guided-tissue regeneration plate support screw. (Gum tissue not shown.)

Figures 7, 8, 9, 10, 11, 12:
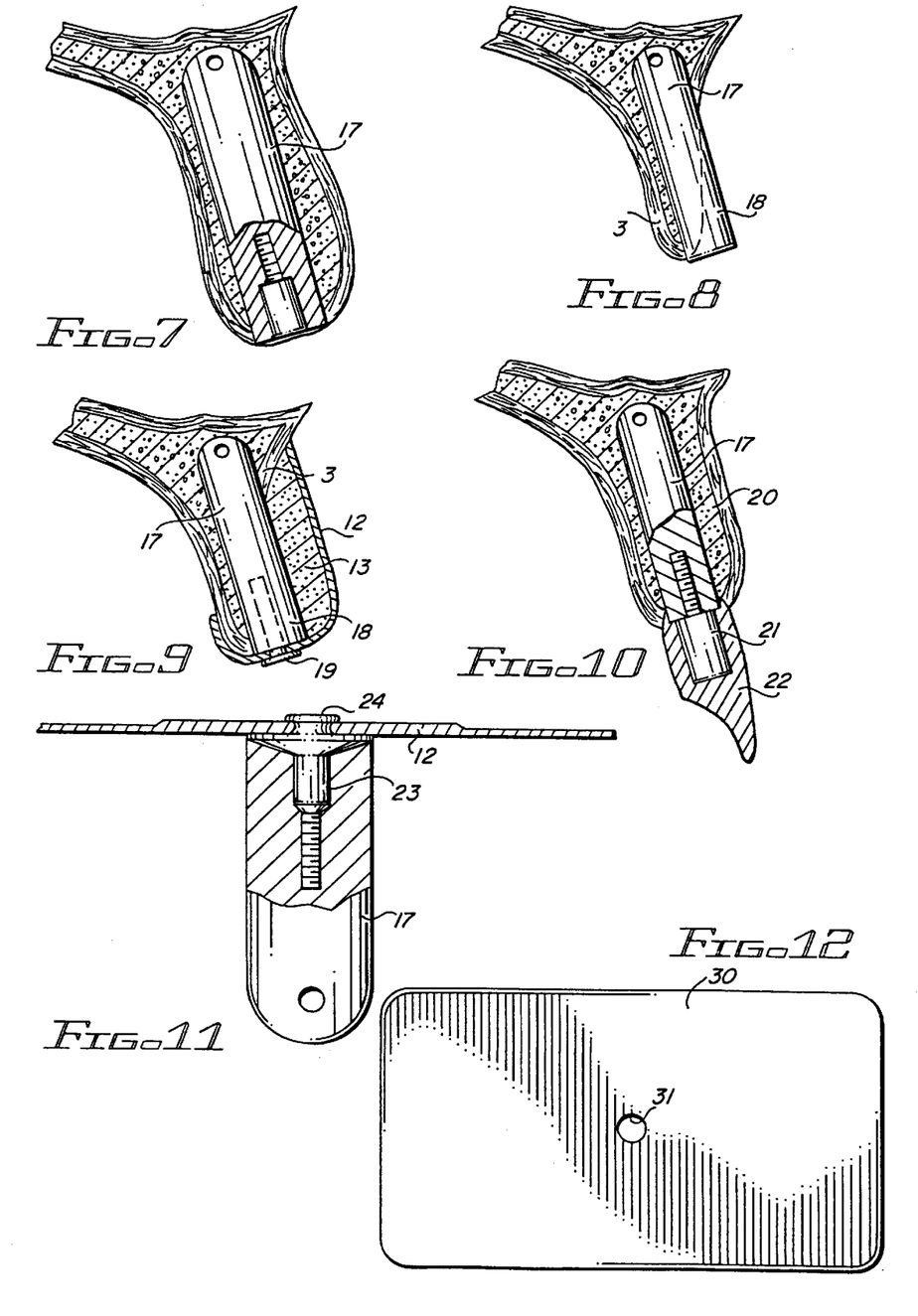
FIG. 7 depicts the placement of a large implant into the new bony ridge.
FIG. 8 shows the placement of an implant into an atrophic bony ridge.
FIG. 9 depicts the installation of a guided-tissue regeneration plate using a screw supplied by an implant manufacturer.
FIG. 10 illustrates the final result of the process shown progressively in FIGS. 8, 9 and 10.
FIG. 11 illustrates the manner in which the guided-tissue regeneration plate can be snap-attached over a modified healing screw made to internally thread into a dental implant.
FIG. 12 depicts a non-perforated embodiment of the guided-tissue regeneration plate.

FIG. 7 depicts the placement of a large implant 17 into the new bony ridge. A tooth can be attached to the implant later.

FIG. 8 shows the placement of an implant 17 into an atrophic bony ridge 3. In this environment, the implant is not fully encased in bone resulting in an exposed area 18 of the implant outside the confines of the existing bone 3.

FIG. 9 depicts the installation of a guided-tissue regeneration plate 12 by inserting the healing screw 19 supplied by the implant manufacturer which can be used in place of a tenting-type support screw to mate the guided-tissue regeneration plate 12 directly to the implant 17. This screw 19 extends through the aperture of the guided-tissue regeneration plate 12 and is thus used instead of the snap-type embodiment previously described. The space 13 created by the guided-tissue regeneration plate 12 is filled with bone graft material, thus covering the exposed portion of the dental implant 18 which is out of the confines of the existing resorbed bony ridge 3.

FIG. 10 illustrates the final result of the process shown progressively in FIGS. 8, 9, 10 after the removal of the guided-tissue regeneration plate (not shown) by revealing that the dental implant 17 is now covered with new bone 20 that has grown around the dental implant after four-to-eight months of healing time and the subsequent removal of the guided-tissue regeneration plate system. As will be apparent to those skilled in the art, after the removal of the guided-tissue regeneration plate, a post has been placed into the dental implant 17 as normal followed by a crown or tooth 22 which is secured to the post in the well known manner.

FIG. 11 illustrates the manner in which the guided-tissue regeneration plate 12 can be snap-attached over a modified healing screw 23 made to internally thread into a dental implant 17. The modified healing screw 23 has a receiver cap 24 adapted to receive the generally centrally disposed aperture in the guided-tissue regeneration plate 12.

FIG. 12 depicts a non-perforated embodiment 30 of the guided-tissue regeneration plate, particularly illustrating the generally central aperture 31 by which the guided-tissue regeneration plate may be secured using a screw as previously described.

Figure 13:
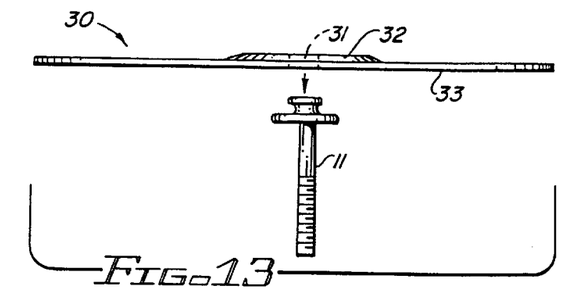
FIG. 13 illustrates a snap configured support screw ready to receive a guided-tissue regeneration plate.

FIG. 13 depicts the snap configured support screw 11 ready to receive the guided-tissue regeneration plate 30 through the aperture 31. Attention is also directed to the cross-section of the guided-tissue regeneration plate 30 which includes a relatively thick central region 32 and a thinner peripheral region 33 as previously described.

Figure 14:
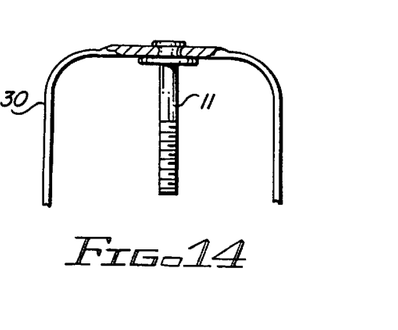
FIG. 14 depicts the guided-tissue regeneration plate over the snap configured support screw after the edges have been bent down to create a space below the guided-tissue regeneration plate.

FIG. 14 depicts the mating of the guided-tissue regeneration plate 30 over the snap configured support screw 11 after the edges have been bent down to create the space below the guided-tissue regeneration plate.

Figure 15:
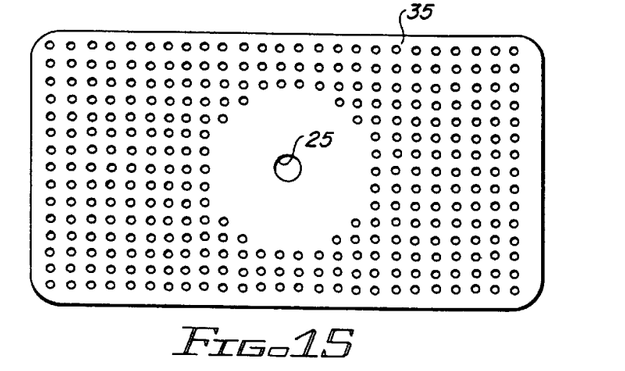
FIG. 15 illustrates a perforated version of the guided-tissue regeneration plate.

FIG. 15 illustrates a perforated version 35 of the guided-tissue regeneration plate which allows for blood supply to pass freely through the plate. Note the generally centrally disposed aperture 25.

Figures 16, 17:
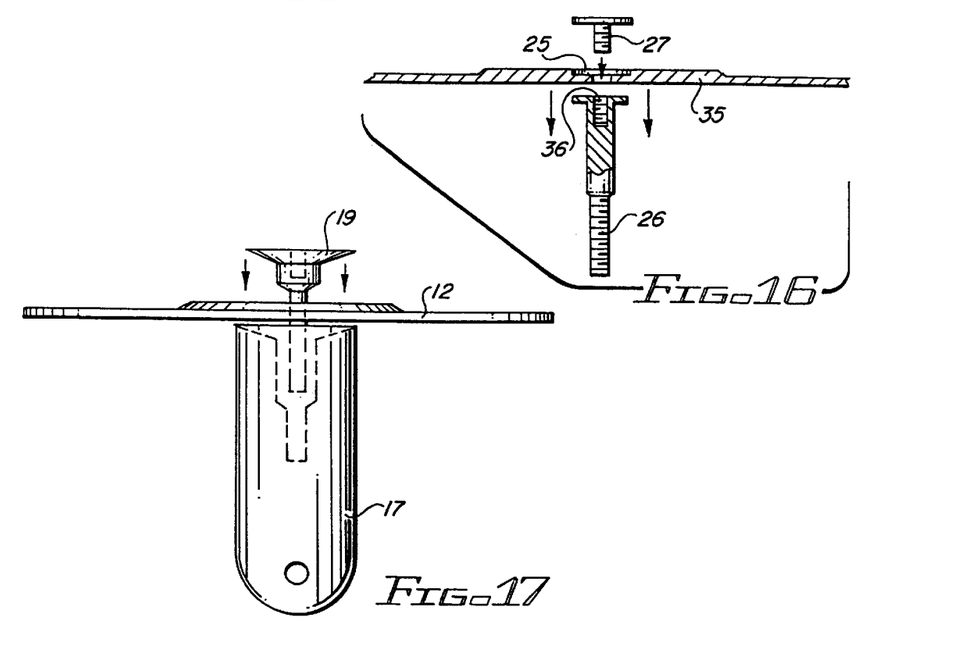
FIG. 16 depicts a guided-tissue regeneration plate being secured to a guided-tissue regeneration plate support screw by a small set screw.
FIG. 17 illustrates the manner in which an exemplary healing screw of the sort typically supplied by a dental implant manufacturer can be employed to secure the guided-tissue regeneration plate to a dental implant.

FIG. 16 depicts a guided-tissue regeneration plate 35 being secured to a guided-tissue regeneration plate support screw 26 by a small set screw 27 which is placed through the aperture 25 in the guided-tissue regeneration plate and into the support screw 26 which has an internally threaded, axially oriented blind hole 36 in its top.

FIG. 17 illustrates the manner in which an exemplary healing screw 19 of the sort typically supplied by a dental implant manufacturer can be employed to secure the guided-tissue regeneration plate 12 to the dental implant 17.

While the guided-tissue regeneration plate system described above has worked well, experience and further development of the fundamental concept has resulted in an alternative preferred embodiment for the guided-tissue regeneration plate component which is discussed below in conjunction with FIGS. 18–21. Thus, referring to FIG. 18, there is shown a guided-tissue regeneration support plate 40 which is a first component of the alternative preferred embodiment for the guided-tissue regeneration plate. The support plate 40 has generally open regions 41, 44 defined, in the exemplary configuration, by integral struts 42 radiating from a central inner support ring 43 to the main body of the support plate. If desired, the central inner support ring 43 and defined space 44 may be dimensioned and configured to serve the same fixation purpose as the apertures 31 and 35 in the respective guided-tissue regeneration plates 30, 35 as described above.

Figures 18, 19:
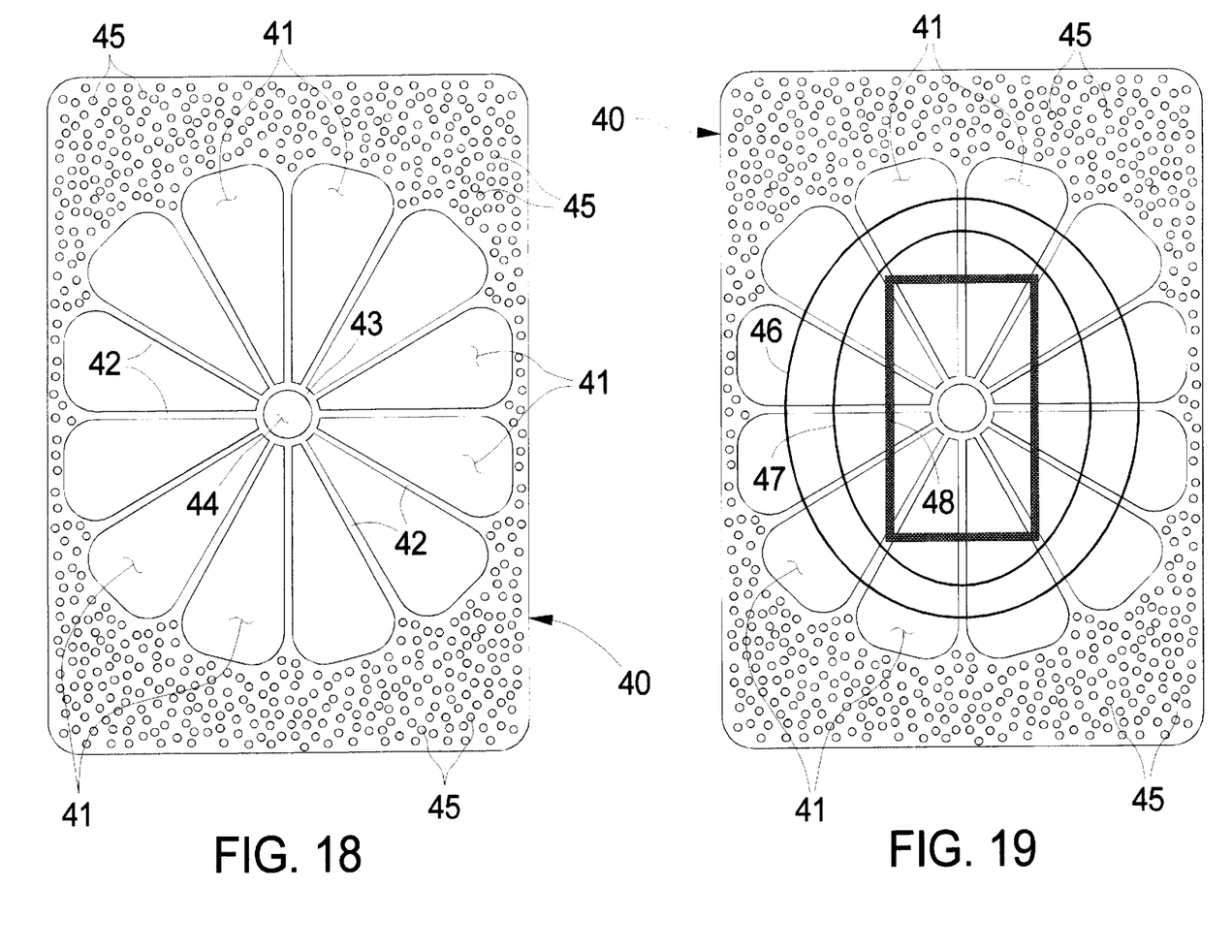
FIG. 18 shows in plan view a guided tissue regeneration support plate used in an alternative preferred embodiment of the invention.
FIG. 19 is a view similar to FIG. 18 illustrating the optional use of stabilizing members added to the central, substantially open region of the support plate.

The main body of the support plate 40, i.e., that portion which is generally outboard the struts 42, the inner support ring 43 and the open regions 41, 44, is somewhat thicker than the guided-tissue regeneration plates 30, 35 previously described. For example, when the presently preferred material, titanium, is used, the thickness of the support plate 40 may be on the order of 0.008–0.025 of an inch and preferably about 0.020 of an inch. The material, as noted with respect to the guided-tissue regeneration plates 30, 35, should be bio-compatible, and other metals which are suitable include chromium cobalt alloy and Teflon-coated surgical steel.

It will be understood that any suitable configuration of the support plate 40 may be employed to provide a peripheral region of sufficient strength and rigidity as to be readily manually shaped to the contours necessary to be fitted to the region above the bony ridge of a given patient as previously described above while providing substantial open regions 41, 44 surrounded by the peripheral region. However, the configuration shown in FIG. 18 has proven to be a good combination of strength and intended purpose. Preferably, in order to both increase the moldability of the support plate 40 and to expose the underlying bone and tissue to the passage of nutrients for the additional reasons discussed above with respect to the guided-tissue regeneration plate 35, numerous perforations 45 are provided in the support plate. Because of the increased thickness of the support plate 40 in comparison to that of the guided-tissue regeneration plate 35, the perforations 45 are preferably mutually closely spaced consistent with not compromising the strength of the support plate.

Referring also to FIG. 19, the struts 42 should be as narrow as reasonably possible while remaining not subject to easy tearing. For example, widths for the struts 42 within the range 0.020–0.030 of an inch, and preferably about 0.025 of an inch, are suitable when the presently preferred material, titanium, is used. Should the central portion still be somewhat weak for the intended purpose (which will become more apparent below), one or more supplementary rectangular struts 48 and/or one or more intermediate, minor struts 46, 47 encompassing the center of the support plate may be fixed to the struts 42 to provide increased rigidity, either on the upper or lower plane of the support plate 40. The widths of the supplementary struts 48 may fall within the same range as those of the struts 42 while the widths or diameters (if titanium wire is used), i.e., the largest transverse dimension, of the minor struts 46, 47 may be smaller yet, falling within the range 0.010–0.020 of an inch, preferably about 0.015 of an inch. The method of fixation of the supplementary strut(s) 47, 47, 48 may be by any suitable expedient such as welding, spot welding, laser welding, adhesive or sintering.

Figure 20:
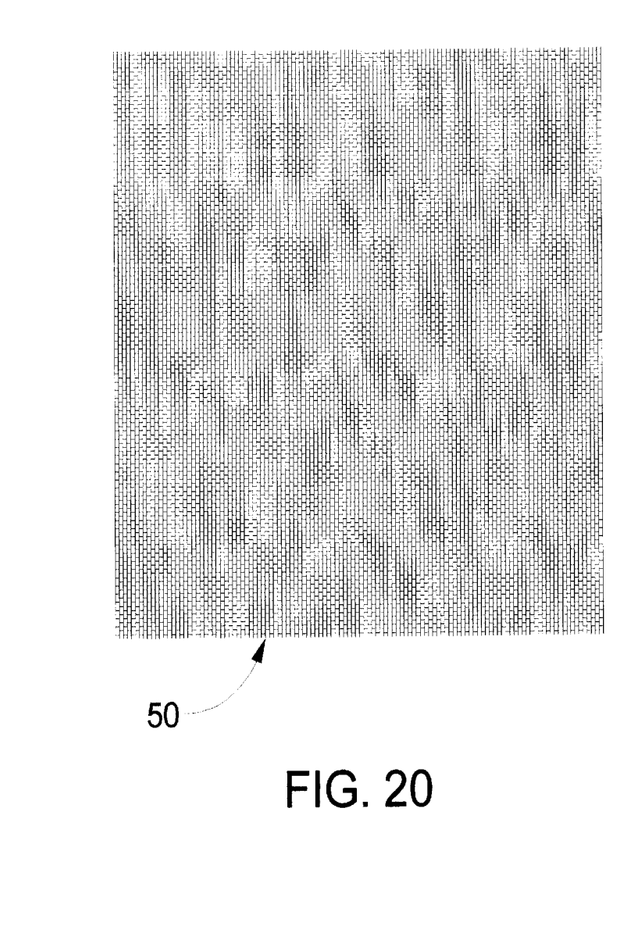
FIG. 20 illustrates a fine mesh screen component used in the alternative preferred embodiment of the invention.
Figure 21:
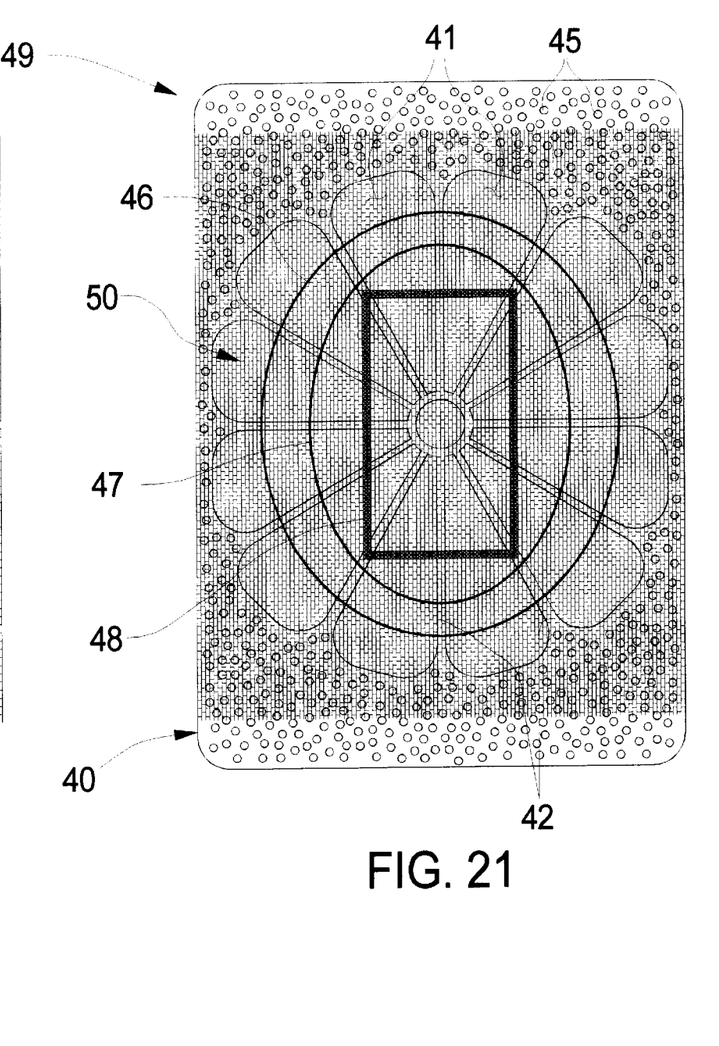
FIG. 21. show a completed guided tissue regeneration plate according to the alternative preferred embodiment of the invention fabricated by integrating the screen shown in FIG. 20 to the support plate shown in FIGS. 18 and 19.

Attention is now directed to FIG. 20 which shows a second component of the alternative preferred embodiment for the guided-tissue regeneration plate. This second component is a fine mesh screen 50. When the presently preferred material, titanium, is used, the diameter of the wire may be in the range of about 0.002–0.006 of an inch, and preferably about 0.003 of an inch disposed in a fine mesh weave on the order of 10×10 wires per inch to 200×200 wires per inch and preferably about 50×50 per inch. Referring also to FIG. 21, the fine mesh screen 50 is juxtaposed onto the support plate 40 generally centrally disposed over the open areas 41 and fixed in place by any means suitable to the material(s) employed. When the presently preferred material, titanium, is used for both components, welding (particularly spot or laser welding), an adhesive or sintering may be employed. Sintering (i.e., heating the complete assembly until the titanium components have fused at the points of abutment) has been found to give particularly good results, and, if the supplementary struts 48 and/or minor struts 46, 47 are employed, they may be integrated into the structure during the same sintering step.

When alternative materials, such as chromium cobalt alloy and Teflon-coated surgical steel, are selected, the size parameters discussed above for titanium are also suitable, and the fixation of the fine mesh screen 50 to the support plate 40 may be carried out in the same manner when chromium cobalt alloy is employed. However, when Teflon-coated surgical steel is used, a compatible fixation method must be employed. For example, the Teflon coating may be first scraped away in the regions of abutment between the two components before the joining step is carried out, or a special purpose adhesive may be used. Preferably, however, the Teflon coating is more practically applied after the two-piece structure has been fabricated.

The resulting two-piece (plus supplementary and/or minor struts) guided-tissue regeneration plate 49 shown in FIG. 21 can then be used in the process described above with notably improved results with respect to the speed and quality with which jaw bone is regenerated along a patient's bony ridge and thicker and more healthy overlying periosteum. Consequently, the long term outlook for the integrity of subsequent dental implants is correspondingly improved, a more satisfactory result having been obtained more quickly.

Figure 22:
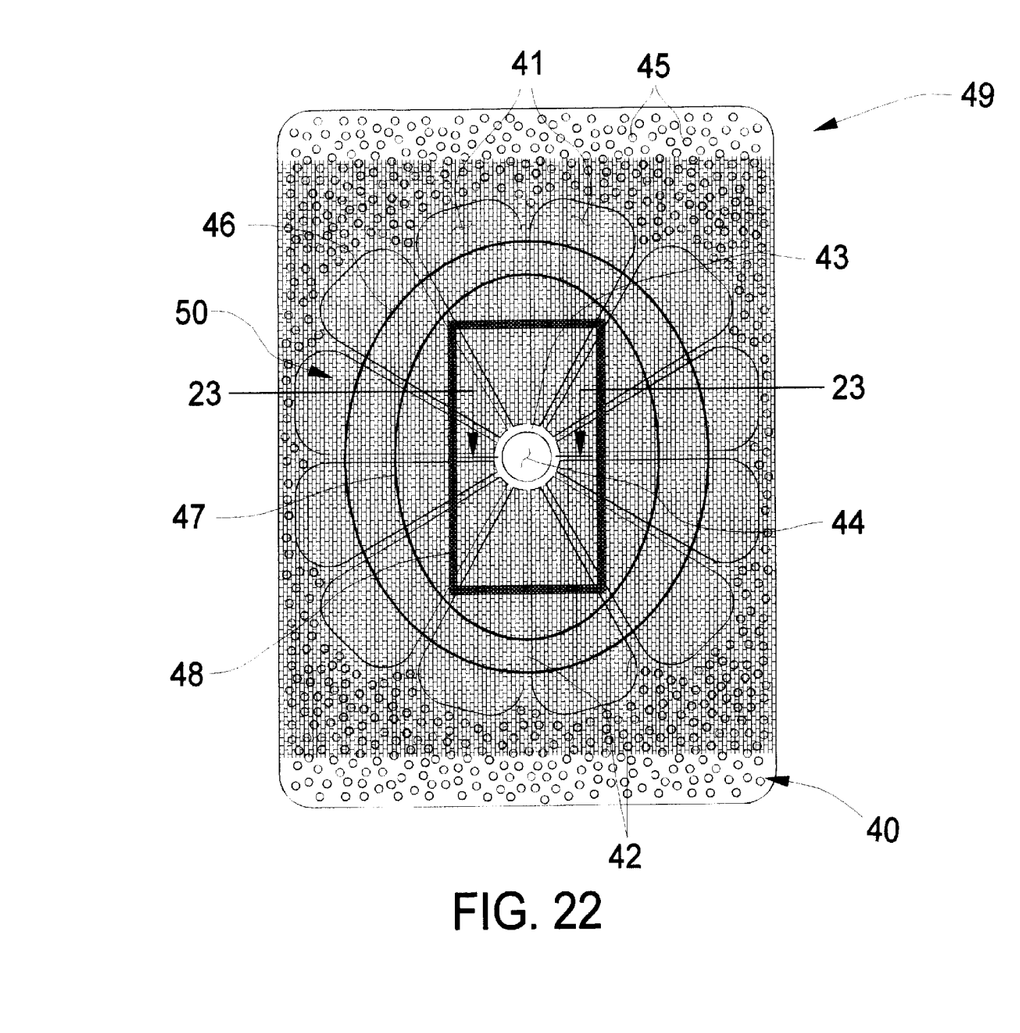
FIG. 22 is a view similar to FIG. 21 illustrating a reinforced central aperture.
Figure 23:
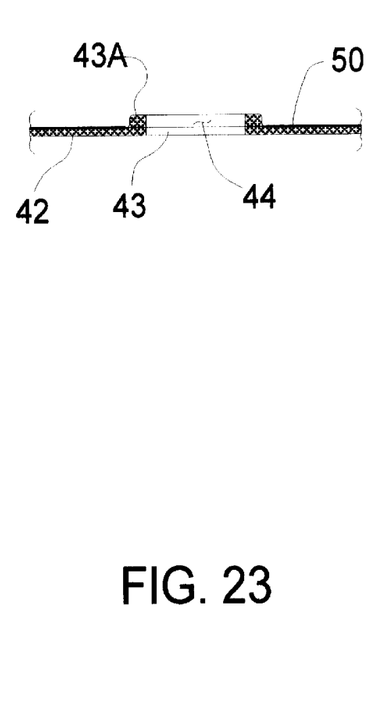
FIG. 23 is an enlarged cross sectional view taken along the lines 23–23 of FIG. 22.

In order to insure a secure fixation of the two-piece guided-tissue regeneration plate 49 to the support structure which is fixed to the jaw bone of a patient as previously described with respect to the guided-tissue regeneration plates 30, 35, it may be usefull to locally reinforce the central inner support ring 43 which defines the central aperture 44 which functionally corresponds to the apertures 31, 25. FIGS. 22 and 23 illustrate a reinforced central inner support ring 43. More particularly, as best shown in the enlarged fragmentary cross section of FIG. 23, the thickness of the central inner support ring 43 may be augmented by any suitable means such as by stacking additional material 43A over the support ring 43 which is integral with the struts 42 as previously described.

Figure 24:
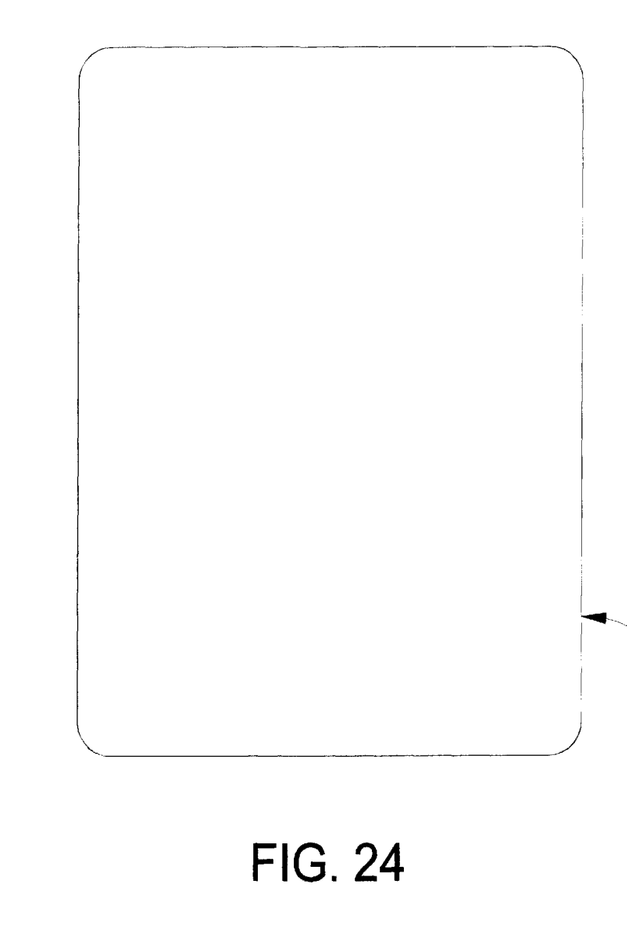
FIG. 24 is a plan view of an imperforate plate used in a variant process for preparing the alternative preferred embodiment of the invention.

Preparation of a variant version of the second preferred embodiment is illustrated in FIGS. 24–27. FIG. 24 shows an imperforate monolithic plate 60 having peripheral outer dimensions corresponding to those of the guided-tissue regeneration plate 49 shown in FIG. 22. As previously mentioned, a preferred material is titanium plate having a thickness of about 0.008–0.025 of an inch and preferably about 0.012 of an inch. The imperforate plate 60 is subjected to further processing to obtain the desired guided-tissue regeneration plate as a unitary structure.

Figure 25:
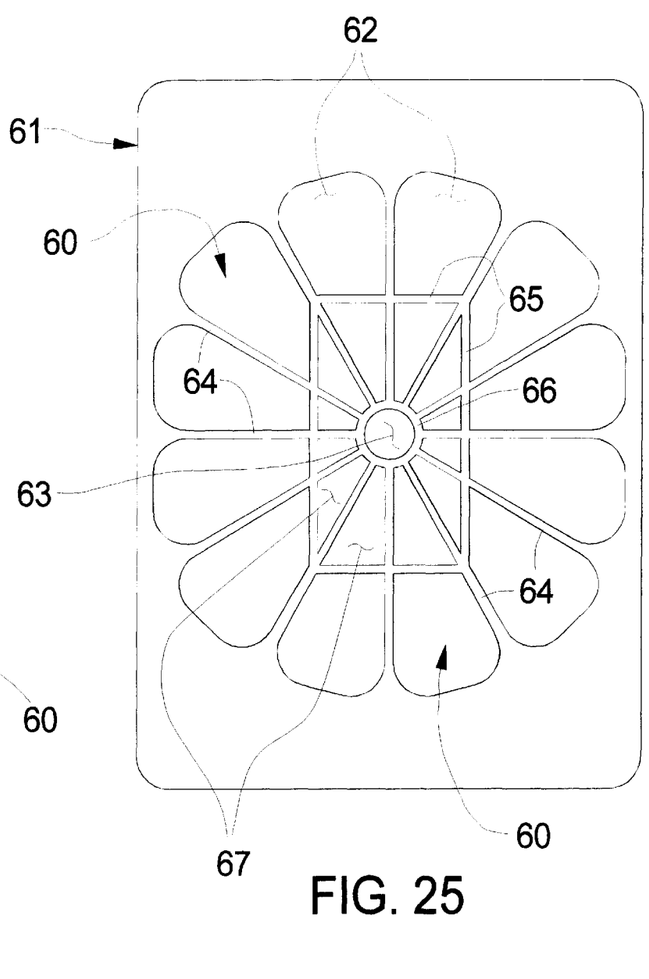
FIG. 25 is a plan view of a mask, overlaying the imperforate plate, used to define predetermined central areas of the imperforate plate to be reduced in thickness.

Thus, referring now to FIG. 25, in anticipation of reducing the thickness of predetermined central regions of the plate 60, a suitable configured mask 61 is prepared and juxtaposed overlaying one surface of the plate. The mask 61 may be a separate stencil-like layer or may be deposited directly on the surface of the plate 60 by a conventional technique such as by depositing a photo-resist layer applied in the desired pattern; i.e., a pattern which will shield the areas of the plate 60 which are not to be reduced in thickness. Accordingly, the areas which are not coated or otherwise masked off are subject to reduction in thickness. Because the open region pattern employed in the example describing the first version of the second preferred embodiment of the guided-tissue regeneration plate has been found to work well, it is also used to describe the second version. Still referring to FIG. 25, radial struts 64 of the mask 61 define a series of circumferentially distributed openings 62 while arms adjoining adjacent radial struts 64 define supplementary struts 65 which corresponds to the supplementary struts 48 shown in FIGS. 19, 21 and 22 and discussed above. The rectangular configuration of the supplementary struts 65 and the inner ends of the radial struts 64 define additional openings 67. The inner ends of the radial struts 64 each terminate at a ring 66 which circumscribes central mask opening 63.

Once the mask 61 has been emplaced over the plate 60, the masked surface can be subjected to a conventional acid etch to remove unprotected metal and hence reduce the thickness of the plate 60 in the unmasked areas to the previously discussed range of 0.002–0.006 of an inch and preferably about 0.003 of an inch. The rate and extent of the metal removal can be controlled, as well known in the art, by selecting the type of acid, its concentration and temperature and the length of time the plate is subjected to the acid.

Figure 26:
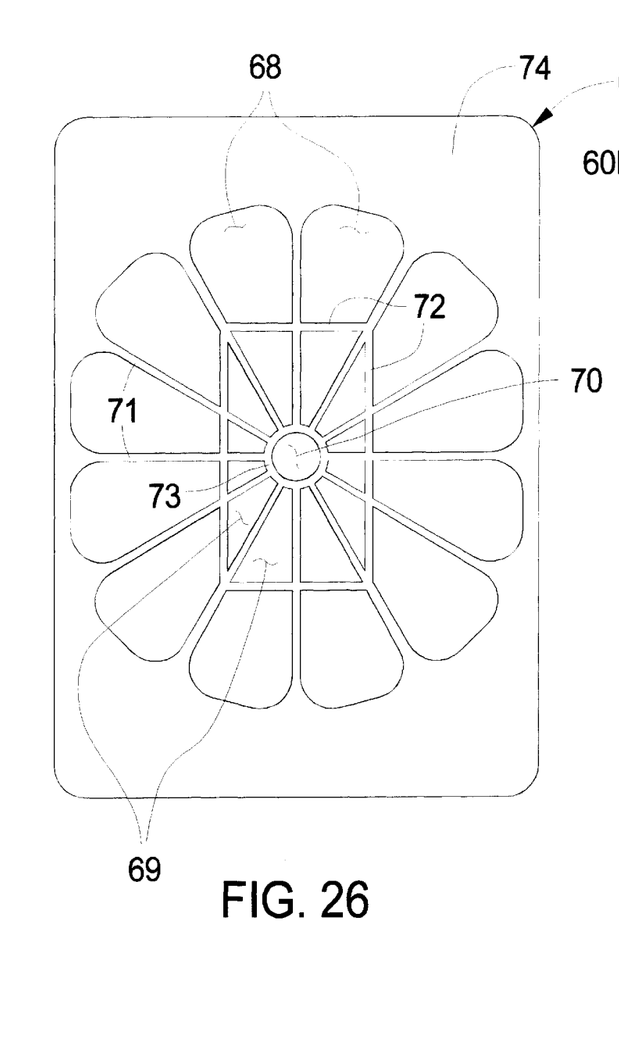
FIG. 26 is a plan view of the imperforate plate after the predetermined central areas have been reduced in thickness.

FIG. 26 shows the plate 60A after the acid etch step has been completed. Thus, regions 68, 69, 70 will be understood to be of diminished thickness while the strut regions 71, supplementary strut regions 72, central ring region 73 and peripheral region 74 remain at the original thickness of the plate because they were protected by the mask during the etching operation.

Figure 27:
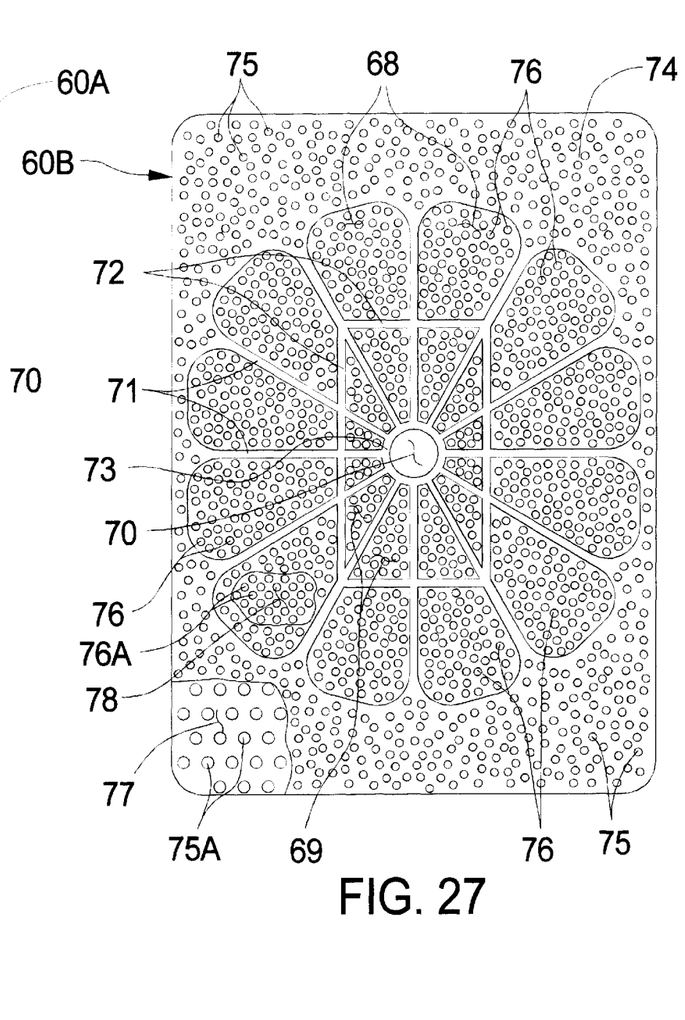
FIG. 27 is a plan view of a completed guided-tissue regeneration plate prepared by the variant process after a perforating step has been carried out.

The second variant of the second preferred embodiment of the guided-tissue regeneration plate is competed by perforating its surface with a large number of closely spaced apertures, typically circular in shape. As shown in FIG. 27, the guided-tissue regeneration plate 60B has been pierced by numerous closely spaced apertures 75 in the regions 71, 72, 73, 74 of the plate which were not reduced in thickness. In the regions 68, 69 which were reduced in thickness, the plate is pierced even more densely with numerous closely spaced apertures 76. The central aperture 70 is opened through the plate 60B during the finishing process to serve as a fixation screw receiving opening in the same manner as previously described with respect to the central aperture 44 (FIGS. 22, 23) of the two-piece first variant of the alternative preferred embodiment for the guided-tissue regeneration plate.

The size and spacing of the apertures in both the original thickness and the reduced thickness regions of the guided-tissue regeneration plate 60B affects both the porosity and the mechanical pliability of the individual regions. The spacing can be either random as shown for the majority of the areas in FIG. 27 or in a definite pattern as shown in the regions 76 (a thinned-down region) and 77 (an original thickness region-not enlarged). The regions 76 and 77 are contrasted by the use of smaller apertures and finer spacing in the reduced thickness region 76, thus achieving increased porosity. In contrast, the larger apertures and wider spacing employed in the original thickness region 77 provides a stiffer, but still compliant, structure for the peripheral region 74 which achieves a structure mechanically well-adapted for emplacement and subsequent maintenance of its position and configuration in use.

It was noted above that one or more minor struts (e.g., the minor struts 46, 47 shown in FIGS. 19, 21) may be provided as necessary to ensure sufficient rigidity to the screened portion of the first variant of the alternative preferred embodiment for the guided-tissue regeneration plate. Corresponding minor struts may also be incorporated into the second variant of the alternative preferred embodiment for the guided-tissue regeneration plate shown in FIG. 27 by either making provision for such in the mask 61 or by later affixing them, as separate components in the manner previously described, to the unitary structure.

While the presently preferred material for either version of the alternative preferred embodiment is titanium, the use of other materials, non-resorptive and resorptive, as discussed above may be employed. As with the previously described embodiments, after the desired bone regeneration has been achieved, the variant preferred embodiment of the guided-tissue regeneration plate may be left in place or removed prior to the implantation process as may be appropriate for a given patient. Further, as also previously described with respect to the guided-tissue regeneration plate 35, if a temporary period of isolation from epithelial cells is desired to create a membrane barrier from epithelial cells for a limited period of time which allows for the exchange of nutrients, ions, and tissue fluid or perhaps blood supply, then a resorptive barrier such as Vicryl™, collagen, resorptive hydroxyapatite crystals or Guidor™ can be applied to the top or bottom side of the guided-tissue regeneration plates 49, 60B to seal the perforations, then resorbing a limited time later after the system is installed.

A performance improving enhancement which can be employed either with the guided-tissue regeneration plate described and claimed in the afore-mentioned parent U.S. Pat. No. 5,839,899 or with the guided-tissue regeneration plates described and claimed herein is to decrease the surface tension, and hence increase the "wetability", of the guided-tissue regeneration plate surfaces. This effect can be achieved in several ways. For example, subjecting the guided-tissue regeneration plate to a plasma spray or gently blasting it with fine to coarse grit abrasive or subjecting it to a suitable acid etchant for a suitable period will achieve the desired result. This slight roughening of the surface of the guided-tissue regeneration plate serves to promote better tissue adhesion and consequently decreases susceptibility to infection or exposure of the plate. In a variant of this enhancement, only the top (tissue side) of the guided-tissue regeneration plate is roughened in order that the tissue will adhere to it, yet the plate can be readily peeled away in due course from the underlying, newly-formed bone.

Thus, while the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, the method comprising:

A) fixing a support medium to the jaw bone, the support medium being configured to receive and support a guided-tissue regeneration plate;

B) positioning the guided-tissue regeneration plate next to the jaw bone in a tent-like manner to create a protected space by affixing the guided-tissue regeneration plate to the support medium, wherein the guided-tissue regeneration plate is pliable and moldable, but keeps its shape after being molded, the guided-tissue regeneration plate being fabricated from a bio-compatible material; and C) waiting for bone to grow in the resulting protected space; the improvement in which:

D) the guided-tissue regeneration plate comprises first and second integrated components including:
1) a first component comprising a support plate having a peripheral region and a generally open central portion extending through the support plate and having a diameter that extends over the majority of a length and/or width of the support plate; and
2) a fine mesh screen positioned over the central portion of the support plate and fixed to the peripheral region thereof.

2. The method of claim 1 in which said support plate and said fine mesh screen are each made of a bio-compatible material selected from the group including titanium, chromium cobalt alloy and Teflon-coated surgical steel and in which said peripheral region of said support plate is perforated.

3. The method of claim 2 in which said guided-tissue regeneration plate is coated with a resorptive, bio-compatible material for the purpose of creating a temporary guided-tissue regeneration plate barrier to prevent migration of epithelial cells across its surface, yet allow blood supply and/or nutrients to pass through the resorptive barrier.

4. The method of claim 3 in which:

A) the thickness of said peripheral region of said support plate falls within the range of 0.008–0.025 of an inch; and B) said fine mesh screen comprises a weave of wire in which:
1) the diameter said wire employed falls within the range of 0.002–0.006 of an inch; and
2) the weave of said wire falls within the range of 10×10 wires per inch to 200×200 wires per inch.

5. The method of claim 2 in which:

A) the thickness of said peripheral region of said support plate falls within the range of 0.008–0.025 of an inch; and B) said fine mesh screen comprises a weave of wire in which:
1) the diameter said wire employed falls within the range of 0.002–0.006 of an inch; and
2) the weave of said wire falls within the range of 10×10 wires per inch to 200×200 wires per inch.

6. The method of claim 5 in which integral struts extend from said peripheral region of said support plate into said generally open central portion thereof to provide support for said fine mesh screen.

7. The method of claim 6 in which at least a plurality of said integral struts join a circular central support having an aperture therethrough for coupling with said support medium.

8. The method of claim 5 in which at least a plurality of said integral struts join a circular central support having an aperture therethrough for coupling with said support medium.

9. The method of claim 2 in which at least a plurality of integral struts join a circular central support having an aperture therethrough for coupling with said support medium.

10. The method of claim 1 in which said guided-tissue regeneration plate is coated with a resorptive, biocompatible material for the purpose of creating a temporary guided-tissue regeneration plate barrier to prevent migration of epithelial cells across its surface, yet allow blood supply and/or nutrients to pass through the resorptive barrier.

11. The method of claim 10 in which:
A) the thickness of said peripheral region of said support plate falls within the range of 0.008–0.025 of an inch; and
B) said fine mesh screen comprises a weave of wire in which:
  1) the diameter said wire employed falls within the range of 0.002–0.006 of an inch; and
  2) the weave of said wire falls within the range of 10×10 wires per inch to 75×75 wires per inch.

12. The method of claim 1 in which:
A) the thickness of said peripheral region of said support plate falls within the range of 0.008–0.025 of an inch; and
B) said fine mesh screen comprises a weave of wire in which:
  1) the diameter said wire employed falls within the range of 0.002–0.006 of an inch; and
  2) the weave of said wire falls within the range of 10×10 wires per inch to 200×200 wires per inch.

13. The method of claim 12 in which integral struts extend from said peripheral region of said support plate into said generally open central portion thereof to provide support for said fine mesh screen.

14. The method of claim 13 in which at least a plurality of said integral struts join a circular central support having an aperture therethrough for coupling with said support medium.

15. The method of claim 12 in which at least a plurality of integral struts join a circular central support having an aperture therethrough for coupling with said support medium.

16. The method of claim 1 in which at least a plurality of integral struts join a circular central support having an aperture therethrough for coupling with said support medium.

17. The method according to claim 1, wherein
at least a first region of the surface of the guided-tissue regeneration plate is roughened to decrease the surface tension thereof.

18. The method of claim 17 in which the entire surface of said guided-tissue regeneration plate is roughened to decrease the surface tension thereof.

19. The method according to claim 1, wherein the support medium comprises a screw and an implant.

20. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, the method comprising:
A) fixing a support medium to the jaw bone, the support medium being configured to receive and support a guided-tissue regeneration plate;
B) positioning the guided-tissue regeneration plate next to the jaw bone in a tent-like manner to create a protected space by affixing the guided-tissue regeneration plate to the support medium, wherein the guided-tissue regeneration plate is pliable and moldable, but keeps its shape after being molded, the guided-tissue regeneration plate being fabricated from a bio-compatible material; and
C) waiting for bone to grow in the resulting protected space; the improvement in which:
D) the guided-tissue regeneration plate comprises first and second integrated components including:
  1) a first component comprising a support plate having a peripheral region and a generally open central portion; and
  2) a fine mesh screen positioned over the central portion of the support plate and fixed to the peripheral region thereof, wherein integral struts extend from said peripheral region of said support plate into said generally open central portion thereof to provide support for said fine mesh screen.

21. The method of claim 20 in which at least a plurality of said integral struts join a circular central support having an aperture therethrough for coupling with said support medium.

22. The method according to claim 20, wherein the support medium comprises a screw and an implant.

23. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, the method comprising:
A) fixing a support medium to the jaw bone, the support medium being configured to receive and support guided-tissue regeneration plate;
B) positioning the guided-tissue regeneration plate next to the jaw bone in a tent-like manner to create a protected space by affixing the guided-tissue regeneration plate to the support medium, wherein the guided-tissue regeneration plate is pliable and moldable, but keeps its shape after being molded, the guided-tissue regeneration plate being fabricated from a bio-compatible material; and
C) waiting for bone to grow in the resulting protected space; the improvement in which:
D) the guided-tissue regeneration plate comprises first and second integrated components including:
  1) a first component comprising a support plate having a peripheral region and a generally open central portion; and
  2) a fine mesh screen positioned over the central portion of the support plate and fixed to the peripheral region thereof;
wherein said peripheral region of said support plate is perforated, and wherein integral struts extend from said peripheral region of said support plate into said generally open central portion thereof to provide support for said fine mesh screen.

24. The method of claim 23 in which at least a plurality of said integral struts join a circular central support having an aperture therethrough for coupling with said support medium.

25. The method according to claim 23, wherein the support medium comprises a screw and an implant.

26. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, the method comprising:
   A) fixing a support medium to the jaw bone, the support medium being configured to receive and support a guided-tissue regeneration plate;
   B) positioning the guided-tissue regeneration plate next to the jaw bone in a tent-like manner to create a protected space by affixing the guided-tissue regeneration plate to the support medium, wherein the guided-tissue regeneration plate is pliable and moldable, but keeps its shape after being molded, the guided-tissue regeneration plate being fabricated from a bio-compatible material; and
   C) waiting for bone to grow in the resulting protected space; the improvement in which:
   D) the guided-tissue regeneration plate comprises first and second regions of a monolithic structure wherein:
      1) the first region comprises a peripheral area having a first thickness; and
      2) the second region comprises a central area extending through the support plate having a thickness which is less than that of the peripheral area, the central area being perforated with a plurality of apertures.

27. The method of claim 26 in which said monolithic structure is made of a bio-compatible material selected from the group including titanium, chromium cobalt alloy and Teflon-coated surgical steel and in which said peripheral region of said support plate is perforated.

28. The method of claim 27 in which:
   A) the thickness of said peripheral area of said guided-tissue regeneration plate falls within the range of 0.008–0.025 of an inch; and
   B) the thickness of said central area of said guided-tissue regeneration plate falls within the range of 0.002–0.006 of an inch.

29. The method of claim 28 in which integral struts extend from said peripheral area of said guided-tissue regeneration plate into said central area to provide support for said central area.

30. The method of claim 29 in which at least a plurality of said integral struts join a circular central support having an aperture therethrough for coupling with said support medium.

31. The method of claim 28 in which at least a plurality of said integral struts join a circular central support having an aperture therethrough for coupling with said support medium.

32. The method of claim 27 in which integral struts extend from said peripheral area of said guided-tissue regeneration plate into said central area to provide support for said central area.

33. The method of claim 32 in which at least a plurality of said integral struts join a circular central support having an aperture therethrough for coupling with said support medium.

34. The method of claim 27 in which at least a plurality of integral struts join a circular central support having an aperture therethrough for coupling with said support medium.

35. The method of claim 26 in which said guided-tissue regeneration plate is coated with a resorptive, bio-compatible material for the purpose of creating a temporary guided-tissue regeneration plate barrier to prevent migration of epithelial cells across its surface, yet allow blood supply and/or nutrients to pass through the resorptive barrier.

36. The method of claim 26 in which said guided-tissue regeneration plate is coated with a resorptive, bio-compatible material for the purpose of creating a temporary guided-tissue regeneration plate barrier to prevent migration of epithelial cells across its surface, yet allow blood supply and/or nutrients to pass through the resorptive barrier.

37. The method of claim 26 in which:
   A) the thickness of said peripheral area of said guided-tissue regeneration plate falls within the range of 0.008–0.025 of an inch; and
   B) the thickness of said central area of said guided-tissue regeneration plate falls within the range of 0.002–0.006 of an inch.

38. The method of claim 37 in which integral struts extend from said peripheral area of said guided-tissue regeneration plate into said central area to provide support for said central area.

39. The method of claim 38 in which at least a plurality of said integral struts join a circular central support having an aperture therethrough for coupling with said support medium.

40. The method of claim 37 in which at least a plurality of integral struts join a circular central support having an aperture therethrough for coupling with said support medium.

41. The method of claim 26 in which integral struts extend from said peripheral area of said guided-tissue regeneration plate into said central area to provide support for said central area.

42. The method of claim 41 in which at least a plurality of said integral struts join a circular central support having an aperture therethrough for coupling with said support medium.

43. The method of claim 26 in which at least a plurality of integral struts join a circular central support having an aperture therethrough for coupling with said support medium.

44. The method according to claim 26, wherein the support medium comprises a screw and an implant.

45. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, the method comprising:
   A) fixing a support medium to the jaw bone, the support medium being configured to receive and support a guided-tissue regeneration plate;
   B) positioning a guided-tissue regeneration plate next to the jaw bone in a tent-like manner to create a protected space by affixing the guided-tissue regeneration plate to the support medium, wherein the guided-tissue regeneration plate is pliable and moldable, but keeps its shape after being molded, the guided-tissue regeneration plate being fabricated from a bio-compatible material; and
   C) waiting for bone to grow in the resulting protected space; the improvement in which:
   D) the guided-tissue regeneration plate comprises first and second regions of a monolithic structure wherein:

1) the first region comprises a peripheral area having a first thickness; and
2) the second region comprises a central area having a thickness which is less than that of the peripheral area, the central area being perforated with a plurality of apertures, wherein said guided-tissue regeneration plate is fabricated by the steps of:

A) overlaying, on a first surface of a monolithic plate, a mask conforming to the shape of said peripheral area such that only an area conforming to the shape of the central area is exposed;

B) etching the first surface of the monolithic plate in the exposed area to diminish the thickness of the monolithic plate in the exposed area; and C) perforating the central area with a plurality of apertures.

46. The method of claim 45 in which the monolithic plate is a titanium plate.

47. The method according to claim 45, wherein the support medium comprises a screw and an implant.

* * * * *